United States Patent
Stipanovic et al.

(10) Patent No.: US 6,315,900 B1
(45) Date of Patent: Nov. 13, 2001

(54) STATIC SEPARATION METHOD USING NON-POROUS CELLULOSE BEADS

(75) Inventors: Bozidar Stipanovic, Lake Forest; William Darwin Garner, Chicago, both of IL (US)

(73) Assignee: Accurate Polymers, Highland Park, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/324,527

(22) Filed: Jun. 2, 1999

Related U.S. Application Data

(60) Provisional application No. 60/087,902, filed on Jun. 3, 1998.

(51) Int. Cl.[7] ............................................. B01D 15/08
(52) U.S. Cl. ............................. 210/198.2; 210/512.1; 210/635; 210/656; 210/659
(58) Field of Search ............................ 210/198.2, 659, 210/635, 656, 512.1

(56) References Cited

U.S. PATENT DOCUMENTS

| | | | |
|---|---|---|---|
| 3,796,634 | 3/1974 | Haynes et al. | 195/63 |
| 4,042,499 | * 8/1977 | Ramstad | 210/659 |
| 4,155,846 | * 5/1979 | Novak | 210/659 |
| 4,238,327 | * 12/1980 | Liburdy | 210/656 |
| 4,631,129 | * 12/1986 | Heikkila | 210/659 |
| 4,780,210 | * 10/1988 | Hsia | 210/638 |
| 4,882,050 | 11/1989 | Kopf | 210/231 |
| 4,885,087 | 12/1989 | Kopf | 210/321.72 |
| 4,894,441 | * 1/1990 | Menicagli | 210/651 |
| 5,049,268 | 9/1991 | Kopf | 210/231 |
| 5,137,819 | 8/1992 | Kilburn et al. | 435/179 |
| 5,194,145 | * 3/1993 | Schoendorfer | 210/651 |
| 5,522,993 | * 6/1996 | Carlsson | 210/198.2 |
| 5,567,615 | 10/1996 | Degen et al. | 435/280 |
| 5,567,617 | 10/1996 | Degen et al. | 435/280 |
| 5,656,373 | 8/1997 | Scarpa et al. | 428/402 |
| 5,866,006 | * 2/1999 | Lihme | 210/198.2 |
| 5,874,006 | * 2/1999 | Lee | 210/651 |
| 6,077,940 | * 6/2000 | Reis | 210/656 |

FOREIGN PATENT DOCUMENTS 41 27 256   2/1993   (DE).

\* cited by examiner

*Primary Examiner*—Ernest G. Therkorn
(74) *Attorney, Agent, or Firm*—Davis Wright Tremaine LLP

(57) ABSTRACT

An affinity separation method and system comprising an affinity separation media with low porosity and low non-specific binding, and a fluid containing a target compound to be isolated which is capable of binding onto the affinity separation media in a fluid mixing loop in a static filtration apparatus. The static filtration apparatus comprises an intermixing-chamber containing a filtration medium wherein a tangential flow is created for intermixing the affinity separation media and target compound in the fluid. The fluid is capable of passing through the filtration medium while the affinity separation media are substantially incapable of passing through the filtration medium. The affinity separation media are separated from the fluid by opening the filtrate outlet so as to allow the fluid to pass through the filtration medium of the static filtration apparatus. The filtrate can be thereby rendering substantially free of the target compound.

17 Claims, 2 Drawing Sheets

STATIC SEPARATION METHOD USING NON-POROUS CELLULOSE BEADS

RELATED APPLICATION

The present application claims the benefit of the filing dates under 35 U.S.C. §119(e) to provisional U.S. Patent Application Ser. No. 60/087,902 filed on Jun. 3, 1998, which is hereby incorporated by reference.

BACKGROUND OF THE INVENTION

Purification systems using glass or metal tubes which contain a packed column of separation medium, for example, beads or particles, are known. These tubes are known as column boxes. Because the separation medium is compacted within the column boxes, the flow rates are slow and the column boxes have a limited capacity. Therefore, prior art purification technology has focused on increasing the porosity of the separation medium to increase the flow rates and capacity within the column box. The object of these known systems is to purify the largest amount of material within the shortest amount of time while keeping the amount of contaminants low and the product yields high. One problem with the old purification technology is that increasing porosity of the separation medium achieved faster flow rates and capacity, but reduced product yields and quality.

A past method, which does not use a column box, utilized a dynamic (i.e., mechanical forces at the site of filtration) filtration system with a variety of separation medium. This old method and apparatus also failed in part because the sheering forces of the dynamic system damaged the separation medium and the bio-compounds being purified.

Prior methods of affinity separation involving dynamic filtration of cellulose and non-cellulose beads have the disadvantage that the beads degrade due to sheering forces inherent in dynamic filtration. These sheering forces irreversibly damage bead supports and the sheer-sensitive biological molecules grafted or bound to them. Generally, many porous beads will fragment due to the agitation and sheering forces contained in the dynamic affinity separation apparatus. The present invention overcomes the disadvantages of the prior art by utilizing a static affinity separation method which is gentle on beads and biological molecules, but causes intermixing of the target compound to be purified with the sheer-sensitive beads and biological molecules which flow through the static tangential flow filters.

The prior art discloses the use of polystyrene beads in dynamic filtration apparatuses for affinity separation of biological compounds. Certain disadvantages are involved in the use of polystyrene beads, such as high non-specific adsorbing of biological molecules on their hydrophobic surfaces. Further, polystyrene beads have open pores on the surface of the bead which entrap contaminants which will co-purify with wanted products and decrease yield and purity of a target compound. Polystyrene has been found to exhibit a high degree of agglomerate and to adhere to the filters used in dynamic affinity separation methods. This agglomeration of the polystyrene beads allows for debris to become trapped and spoils the filtration affinity system by clogging the filter. A preferred embodiment of the present invention overcomes the disadvantages of the prior art by adding a multitude of linkers to the bead surface to increase bead coating. Bead coating reduces unwanted agglomeration and filter clogging. This multitude of linkers reduces agglomeration and non-specific binding, resulting in increased stability and reduced entrapment of unwanted contaminants, while enabling the attachment of the target compounds desired to be separated.

The prior art discloses the use of cellulose in dynamic filtration apparatuses for affinity separation of biological compounds. The prior art cellulose particles available are highly porous particles which exhibit entrapment of target and contaminants. Moreover, these highly porous prior art cellulose particles can swell from 25% to 400% of their original size in aqueous medium. Additionally, the prior art cellulose particles are highly sensitive to sheering forces, thus resulting in fragmentation in a dynamic filter. The present invention uses non-porous cellulose beads in a static tangential flow system to prevent bead fragmentation.

BRIEF SUMMARY OF THE INVENTION

A preferred embodiment of the present invention provides an improved affinity separation method and system comprising an affinity separation media with low porosity and low non-specific binding, and a fluid containing a target compound to be isolated which is capable of binding onto the affinity separation media in a fluid mixing loop in a static filtration apparatus. The static filtration apparatus comprises an intermixing-chamber containing a filtration medium having upstream and downstream sides, an inlet in fluid communication with the upstream side of the filtration medium, and a filtrate outlet in fluid communication with the downstream side of the filtration medium, wherein a tangential flow is created for intermixing the affinity separation media and target compound in the fluid. The fluid is capable of passing through the filtration medium while the affinity separation media are substantially incapable of passing through the filtration medium. The affinity separation media are separated from the fluid by opening the filtrate outlet so as to allow the fluid to pass through the filtration medium of the static filtration apparatus. The filtrate can be thereby rendered substantially free of the target compound. If the recovery of the target compound is desired and/or if the affinity separation media are to be reused, the affinity separation media are then thoroughly washed, and the target compound is eluted from the affinity separation media, filtered, and ultimately the target compound is recovered from the filtrate and the affinity separation media may be reused.

The preferred invention apparatus and system ideally utilizes small, reconstituted cellulose particles having no pores and low non-specific binding properties. The cellulose particles of the preferred embodiment of the present invention consist of small, substantially spherical bodies with a near complete absence of irregularities, holes, cracks and the like. The cellulose bodies are made from viscose. This improvements results in uncross-linked, high density, spherical cellulose separation support beads without substantial holes, voids or craters on their surface. In certain circumstances, as where ligands are attached to the cellulose particles, chromatographic separation may be optimized when substrate/sorbent interactions take place exclusively on the outside surface of the particle. In such cases, any presence of holes of a size that may accommodate a substrate molecule cannot be tolerated; otherwise diffusion based interferences may adversely effect resolution of pure compounds.

The cellulose beads are essentially non-crystalline. Electron micrograph sections of the particles mounted in an epoxy matrix display a structure whereby the cellulose particles show a dense non-porous outer shell with an approximate thickness of 1,000 to 2,000 angstroms and a more porous interior of the closed-cell type. The shape of the particles is essentially spherical. The cellulose particles are essentially non-swellable and stable in pH range between about 1 and 13.

The current invention relates to a unique and novel method which eliminates the column box and utilizes low porosity. The present method for the affinity separation of bio-compounds uses a static filtration system instead of the column box to achieve flow rates of liters per minute instead of milliliters per minute, which is typical of high porosity separation media. Therefore, a low porosity, low non-specific binding separation medium, generally the lowest being reconstituted cellulose affinity particles, is preferred.

An advantage of the present inventive method is the provision of the exceptionally efficient separation through an affinity separation procedure of a compound from a dilute solution. A preferred embodiment of the present invention provides a means for lessening the number of processing steps required to perform an affinity separation as compared to known affinity separation methods, thereby increasing the overall yield of the separation method.

A further advantage of the preferred embodiment of the invention is that the present inventive method is able to be conducted in a relatively lesser amount of time as compared to known affinity separation processes.

Moreover, a further advantage of the invention is that since the present inventive method preferably utilizes nonporous affinity particles, the present invention avoids those problems attendant the use of highly porous affinity particles, e.g., fragility during mechanical agitation, affinity particle fouling, susceptibility to crushing, and swelling.

In addition, it is yet another advantage of the invention that the present inventive method generally avoids problems associated with channeling and filtration medium fouling associated with conventional chromatographic affinity separation methods using column boxes.

An embodiment of the present invention overcomes the disadvantages of the prior art by adding a multitude of linkers to the bead surface to coat the bead. Thereby, the bead pores are covered, thus reducing unwanted porosity and non-specific binding which may allow for entrapment and adsorption of unwanted contaminants. The linkers may be added to the beads by covalent bonding or in other manners known to those skilled in the art. This linker coating enables the attachment of special chemical "hooks" which specifically bind the desired target compounds to be separated.

A further advantage of a preferred embodiment of the present invention over the prior art is that the use of reconstituted cellulose particles prevents the entrapment of target molecules and contaminants and the swelling associated with the use of prior art cellulose beads. In comparison, a reconstituted cellulose particle swells no more than 15% of its original size.

A further advantage of a preferred embodiment of the present invention over the prior art is that static tangential affinity systems prevent the accumulation of debris and beads that usually connect and clog tangential flow systems that may get trapped in systems such as the prior art dynamic systems.

DETAILED DESCRIPTION OF THE DRAWINGS AND PREFERRED EMBODIMENTS OF THE INVENTION

Figure 1:
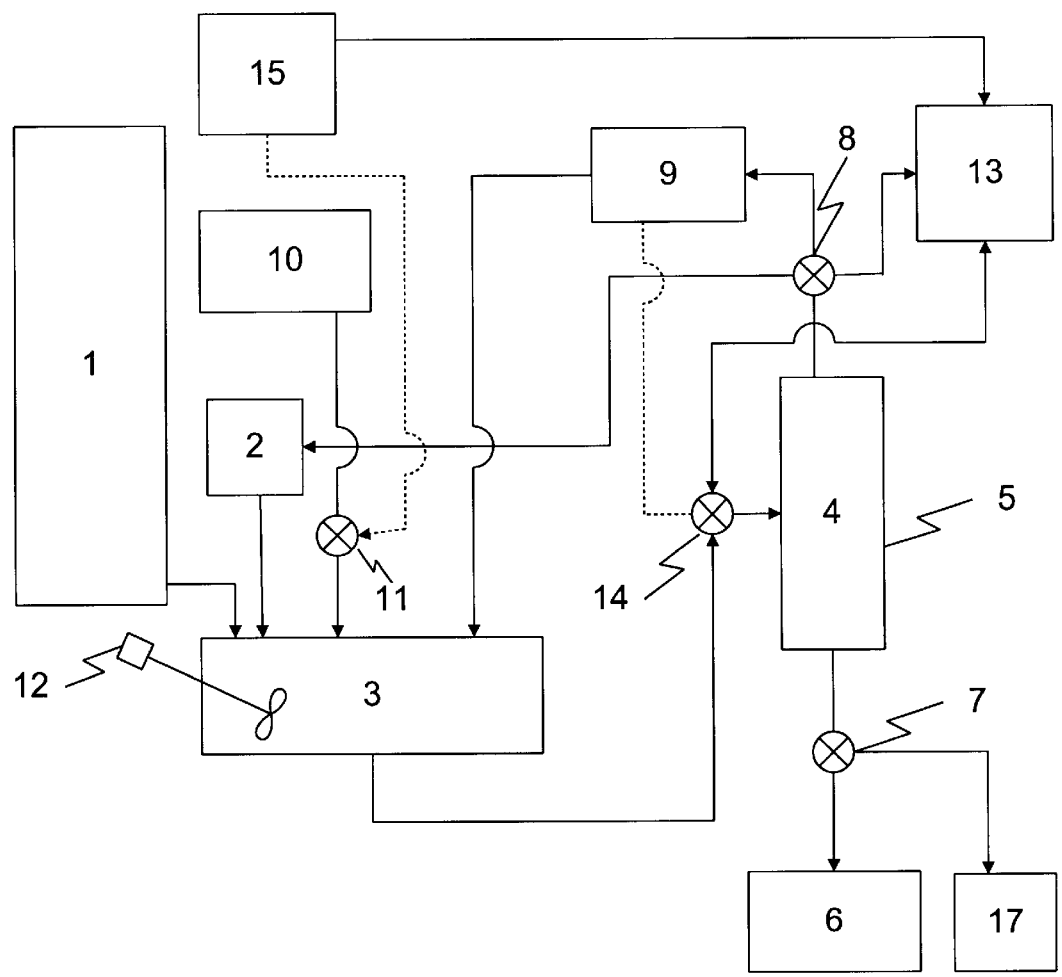
FIG. 1 is a schematic depiction of the significant elements used in a preferred embodiment of the present invention.

The present invention provides an improved affinity separation method. It has been found that the use of a static filtration apparatus having a tangential flow can be used to efficiently effect separation between a fluid without plugging the filter and suspended therein affinity particles. The static filtration apparatus can thereafter be used to separate the fluid from the nonporous cellulose affinity particles having the bound or complexed target thereon. Such a process enables the use of nonporous cellulose affinity particles having small diameters and relatively large surface areas per weight of the cellulose.

The preferred inventive method is an improved affinity separation method comprising:

(a) introducing reconstituted cellulose affinity particles into a fluid containing a target compound to be isolated which is capable of specifically binding onto the cellulose affinity particles by means of specific "hooks" which specifically bind the target compound, (b) filtering the resulting suspension in a static filtration apparatus, comprising a filtration medium having upstream and downstream sides, an inlet in fluid communication with the upstream side of the filtration medium, and a filtrate outlet in fluid communication with the downstream side of the filtration medium, wherein the apparatus has a tangential flow and the fluid is capable of passing through the filtration medium and the nonporous cellulose affinity particles are substantially incapable of passing through the filtration medium, and (c) separating the cellulose affinity particles from the fluid by opening the filtrate outlet so as to allow the fluid to pass through the filtration medium of the static filtration apparatus.

As a consequence of affinity of the target compound for the bead surface, which has been rendered attractive to the target compound, the target concentration in the fluid can be brought down to sufficiently low levels, allowing such process to be used as a practical industrial method of separation of individual compounds from a mixture of a multitude of compounds in a solution.

The relative sizes of the largest debris in the fluid to be treated, the pores of the filtration medium, and the diameter of the reconstituted affinity particles are important in the practical utilization of the present inventive affinity separation method. Ideally, the filtration medium will allow all of the fluid (including the largest debris) to pass therethrough, while preventing any of the reconstituted cellulose affinity particles from passing therethrough. The filtration medium, therefore, will preferably have an average pore size at least a factor of two, and preferably a factor of five or ten, larger than the largest debris in the fluid to be treated, and the reconstituted cellulose affinity particles will preferably be at least a factor of two, and preferably a factor of five or ten, larger than the pore size of the filtration medium. Thus, for example, if the largest debris in the fluid to be treated is in on the order of about 0.1–0.2 micron, the average pore size of the filtration medium will preferably be on the order of about 1–3 microns, while the reconstituted cellulose affinity particles will preferably be on the order of about 10–20 microns.

In general, the smallest acceptable reconstituted cellulose affinity particles, e.g., reconstituted cellulose affinity particles of 60 microns diameter or less, particularly reconstituted cellulose affinity particles of 20 microns diameter or less, are preferably used to improve the recovery of the target compound by increasing the available surface area per unit of weight of the reconstituted cellulose affinity particles for interaction with the fluid being treated. The range of size for the reconstituted cellulose affinity particles can range from nano-size to 120 microns. Accordingly, while pretreatment of the fluid to be treated may not be the most desirable inasmuch as it adversely impacts on the recovery of the target compound by introducing an add additional processing step, there may be instances in which the recovery loss resulting from pretreatment, particularly prefiltering and/or homogenization to reduce the sizes of the largest debris in the fluid, will be more than offset by the resulting ability to use smaller affinity particles having a higher area per unit of weight of the affinity particles.

Although several separation media may be modified to yield affinity beads which possess low porosity and reduced nonspecific binding, the preferred embodiment includes nonporous cellulose beads with reduced nonspecific binding. The reconstituted cellulose affinity particles comprise a spacer and a ligand on the surface thereof which is capable of binding to the target compound in a fluid so as to enable the separation of that compound from the remainder of the fluid. Then, the target compound is capable of being removed from the reconstituted cellulose affinity particles by changing the conditions of the solution, for example, pH, salts, and others. The affinity ligands used to separate particular compounds from a fluid will vary. The proper selection of the ligand will ensure that the target compound selectively and reversibly binds, e.g., complexes with or adsorbs onto, the reconstituted cellulose affinity particle.

In a preferred embodiment, low porosity, low non-specific-binding separation media includes low porosity linker coated polystyrene carbohydrate, glass, porcelain, ceramics, and other low porosity beads known to one skilled in the art. Examples of beads which may be used in the present invention are disclosed in U.S. Pat. No. 5,567,615 to Degan et al. the entire disclosure of which is incorporated herein by reference. In yet another preferred embodiment, the separation medium includes reconstituted, nonporous cellulose particles. In this embodiment, reconstituted cellulose particles exhibit pore-free surfaces with linkage and functional groups in the bulk of the solution free to form attachments to the target compounds that are desired to be separated. The reconstituted cellulose particles have no pores which open onto the particle surface into which may be trapped a target compound to be separated, thereby lowering yield. Further, cellulose particles can be constructed to be of consistent, small size which provides for increase in surface area of contact and a uniform flow in the affinity separation apparatus.

Fusion proteins, where a target protein or a peptide is fused with segments such as glutathion transferase or polyhystidine, require grafted affinity ligands, glutathion, or chelated metals, such as Nickel or Zinc, respectively. In an embodiment of the invention, affinity separation of fusion proteins uses ungrafted cellulose beads of the present invention, without spacers or ligands, for separation of fusion proteins comprising a cellulose binding protein segment fused with a target protein or peptide. In this particular case, the cellulose surface of the beads as a whole represent an affinity site for attaching said cellulose binding protein segment.

The reconstituted cellulose affinity particles preferably have a surface which is smooth and nonporous and are nearly identical.

The reconstituted cellulose affinity particles are preferably substantially spherical shaped. Moreover, the reconstituted cellulose affinity particles are preferably of narrow distribution in diameter. Such reconstituted cellulose affinity particles generally will have the lowest probability of creating flow problems and will allow an easy selection of membrane porosity for fast and clean separation.

The reconstituted cellulose affinity particles may be of any suitable size. The average diameter of the reconstituted cellulose affinity particles will typically be less than about 120 microns, and more usually less than about 60 microns. Preferably, the affinity particles will have an average diameter of less than about 20 microns, and more preferably less than about 10 microns. For many uses, the reconstituted cellulose affinity particles will advantageously have a diameter of about 1 to about 5 microns. The reconstituted cellulose affinity particles preferably have a narrow diameter distribution.

The preferred particles of the present invention are of about 1–3 microns in diameter. Such small particles have relatively high surface area per unit volume and are easily filtered in a static filter apparatus. The efficiency of the overall affinity separation method of the present invention is high because the near complete recovery of the reconstituted cellulose affinity particles with the bound target compound is achieved.

The surface of the preferred cellulose beads has low or no affinity for the target compound in the fluid being treated. Such a surface ensures that the target compound will reversibly complex or otherwise attach exclusively to the ligand on the surface of the particles rather than the surface of the particles itself, where other components or compounds as well might get nonspecifically bound, thereby causing impurities to be present with the target compound. Moreover, the surface of the substrate is preferably smooth to minimize adherence of material other than the target compound to the attached ligand on the surface of the reconstituted cellulose affinity particles and to provide for easy cleaning of the reconstituted cellulose affinity particles. The beads are preferably capable of being reused many times and are chemically and mechanically stable such that the beads do not decompose or otherwise pose contamination problems.

There are potentially endless numbers of ligands for affinity separation of a given target compound. To mention a few generally applicable examples, antibodies of the monoclonal and polyclonal kind, active site analogs, chelated metals, particularly Nickel, Zinc, and Copper are used in the present art as affinity ligands.

The filtration medium used in conjunction with the static filtration apparatus can be any suitable filtration medium and will typically be a porous membrane, preferably a microporous polymeric membrane. While the filtration medium may have any suitable pore rating, e.g., on average of about 20 microns or less, on average of about 10 microns or less, on average of about 5 microns or less, or even about on average of 1 micron or less, the filtration medium will preferably allow for all, or at least substantially all, of the fluid being treated to pass through the filtration medium while retraining all or at least substantially all, of the reconstituted cellulose affinity particles. Thus, the pore rating of the filtration medium is largely dependent on the size of the reconstituted cellulose affinity particles and the size of the largest debris (i.e., nontarget compound and/or particulate) in the fluid being treated.

Figure 2:
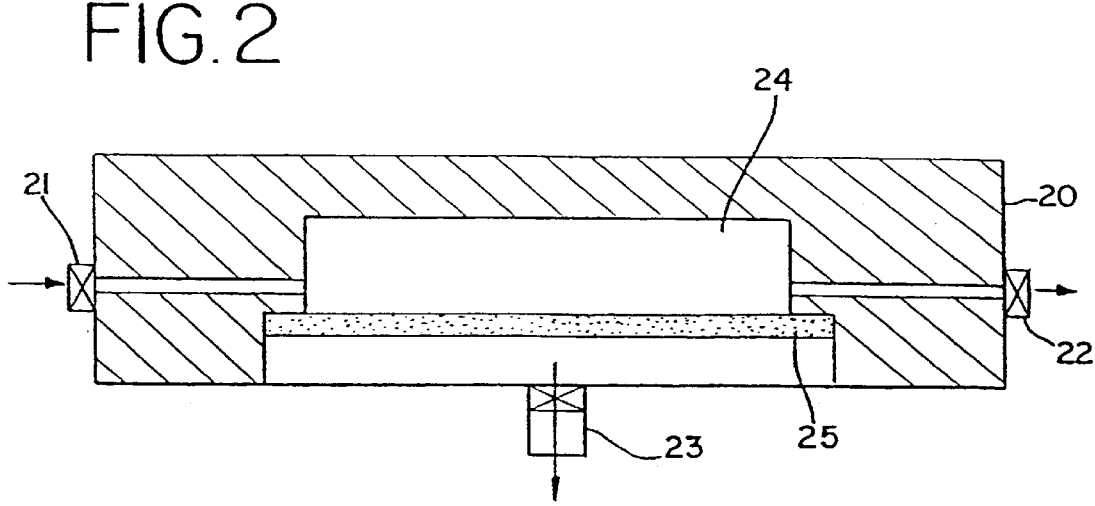
FIG. 2 is a schematic depiction of a preferred embodiment of the apparatus of the present invention for use with the low porosity, low non-specific binding separation media, the preferred separation media being reconstituted cellulose particles.

FIG. 2 schematically depicts a preferred static filtration apparatus for use with the present inventive affinity separation method. The static filtration apparatus comprises a housing 20 having a feed port 21, a concentrate port 22, and a filtrate port 23. A filtration medium or membrane 25 is disposed within the housing 20. The feed port 21 and concentrate port 22 are in fluid communication with the upstream side of the filtration medium 25, while the filtrate port 23 is in fluid communication with the downstream side of the filtration medium 25. Fluid is capable of passing through the filtration medium 25, while the reconstituted cellulose affinity particles are substantially incapable of passing through the filtration medium 25.

In use, a mixture of the fluid containing the target compound and the reconstituted cellulose affinity particles are fed into the housing 20 of the static filtration apparatus via feed port 21 in such a manner as to produce a tangential flow.

The mixture is then filtered through filtration medium 25 by opening filtrate port 23 to allow the fluid to be removed from within the static filtration apparatus. Washing buffer may be introduced into the static filtration apparatus via feed port 21 to remove any unbound material within the static filtration apparatus, and the washing buffer may then be allowed to pass through the filtrate port 23. Multiple washing steps, if desire, can be carried out in the same manner.

Eluent is then introduced, via feed port 21, to detach the target compounds from the reconstituted cellulose affinity particles. After the target compound has been removed from the reconstituted cellulose affinity particles and recovered, the reconstituted cellulose affinity particles can then be reused after washing. The washing buffer is removed by way of port 23.

FIG. 2 is merely a schematic illustration of a preferred embodiment of the apparatus useful in the carrying out of the present inventive method, and particular aspects of an actual apparatus for use with the present invention may vary considerably.

EXAMPLE 1

The present invention may be further understood with reference to the accompanying drawings. FIG. 1 schematically depicts the significant elements used in a preferred embodiment of the present invention. Upon commencement of the present inventive methods, the fluid to be treated, which contains the target compound to be separated from the remainder of the fluid, resides in holding tank 1, while the affinity particles reside in holding tank 2. Both the fluid and the affinity particles are transferred to a buffer tank 3 where they are combined to form a mixture. The mixture is then transferred to the static filtration apparatus 4 via valve 14 and inlet 5, although the fluid and reconstituted cellulose affinity particles could be directly transferred to the static filtration apparatus 4 without passing through the buffer tank 3. The mixture is maintained in the static filtration apparatus 4 without any of the fluid passing through the filtration medium of the static filtration apparatus 4, by, for example, the filtrate valve 7 being in the closed position. Intermixing of the fluid and the reconstituted cellulose affinity particles is provided by an optional agitator 12 or by a tangential fluid in tank 3.

Thereafter, some or all of the mixture is transferred via concentrate valve 8 in a batch or continuous (in-line) process to a detection tank 9, wherein the concentration of the target compound in the fluid which remains unbound to the reconstituted cellulose affinity particles is determined. In a permanent manufacturing process wherein similar batches of fluid are being repeatably treated, there may be no need for any detection means after determining an appropriate quantity of fluid, reconstituted cellulose affinity particles, and residence time in the static filtration apparatus inasmuch as the present inventive method is quite consistent and reproducible as regards the recovery of the target compound.

When it is determined, by whatever means, that a sufficient amount of target compound has been adsorbed onto the reconstituted cellulose affinity particles, then the filtrate valve 7 is opened so that the fluid passes through the filtration medium of the static filtration apparatus 4 into waste tank 6, thereby leaving the reconstituted cellulose affinity particles in the static filtration apparatus 4. The filtration valve 7 is then typically closed, although, alternatively, additional fluid can be passed into the static filtration apparatus 4 for contacting with the reconstituted cellulose affinity particles, particularly if the reconstituted cellulose affinity particles are not saturated with the target compound. Such additional fluid can be passed into the static filtration apparatus 4 in a continuous or semi-continuous manner while some of the fluid in the static filtration apparatus 4 continues to pass through the filtration medium of the static filtration apparatus 4.

After the addition of fluid into the static filtration apparatus 4 is complete and the fluid within the static filtration apparatus 4 has passed through the filtration medium, the washing buffer valve 11 is opened to allow for washing buffer from washing buffer tank 10 to enter the static filtration apparatus 4. The washing buffer is allowed to intermingle with the reconstituted cellulose affinity particles for a suitable period of time, and then the filtrate valve 7 is again opened to allow for the washing buffer to pass to the waste tank 6. Typically, there will be several such wash cycles to ensure that the fluid being treated, except for the target compound bound to the reconstituted cellulose affinity particles, has been removed from the static filtration apparatus 4.

The reconstituted cellulose affinity particles are then transferred to the elution receptacle 13 via the concentrate valve 8. Such a transfer may be accomplished by using washing buffer from the washing buffer tank 10 to transport the reconstituted cellulose affinity particles to elution receptacle 13. Eluent from eluent tank 15 then contacts the affinity particles in the receptacle 13 to detach the target compound from the reconstituted cellulose affinity particles and passes the target compound, together with beads, back into the static filter 4 via valve 14 and inlet 5. The effluent stream exits the static filter via valve 7 and is diverted into tank 7. An optional effluent detection means which monitors the level of a target compound in the effluent stream may also be installed, similar to detection tank 9.

The reconstituted cellulose affinity particles, which no longer have the target compound bound thereto, can consequently be washed and then reused. After washing with buffer from tank 10, regenerated beads are transferred back to tank 2 via concentrate valve 8.

FIG. 1 is merely a schematic illustration of a preferred embodiment of the present invention, and the actual equipment and its placement may be varied considerably for the embodiments of the present invention.

EXAMPLE 2

Figure 3:
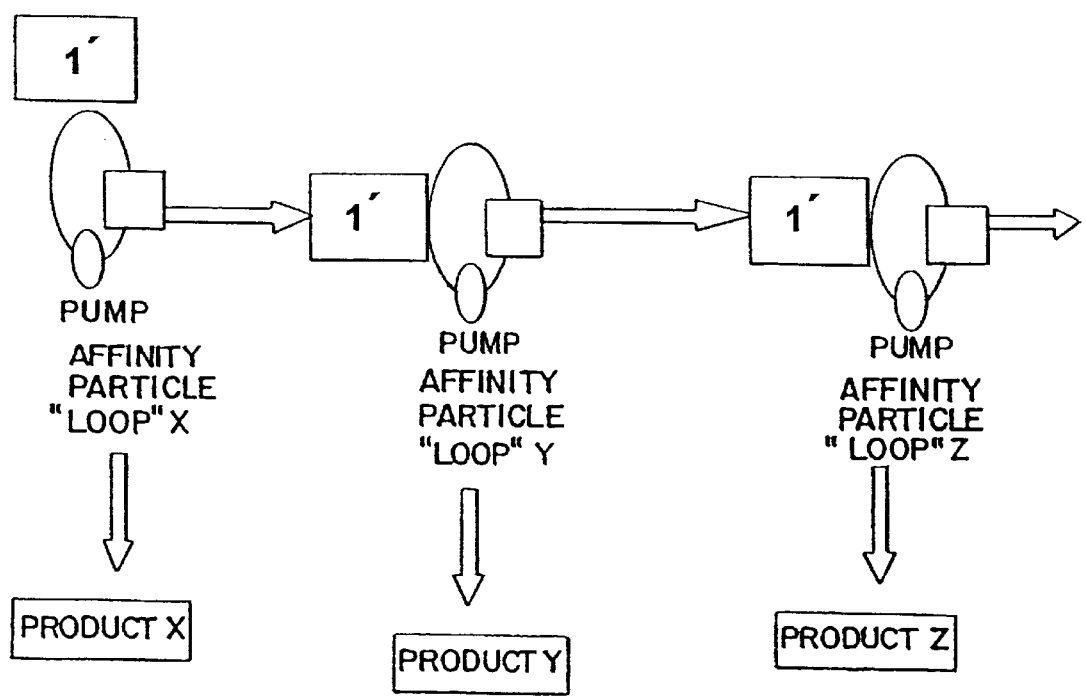
FIG. 3 is a schematic depiction of an embodiment of the present invention for sequential purification of biomaterials.

As shown in FIG. 3, Example 2 comprises a series of purification loops, each of which is a self contained purification system for a particular target, e.g., a biomaterial. The purification loops are connected, enabling the fluid, or permeate of the previous system to be the "feed stock" or fluid to be treated, for the next loop. Each loop may contain affinity particles possessing different hooks or the same hooks as the previous purification loop in the connected configuration. The loops begin with a feed tank 1' which may be similar to the holding tank 1 of FIG. 1. Each loop of affinity particle may purify a specific product from a single source of fluid to be treated which comprises a mixture of products. For example, commonly human immunoglobulin, human albumen, and human clotting factors are purified from raw human plasma by separate methods. Some of these methods in some cases damage the raw human plasma, thus preventing additional product extraction. The current invention describes a method which enables extraction of two or more valuable bio-products from human plasma without damaging the biomaterials within the used raw human plasma. FIG. 3 shows the sequential tangential flow systems where the first system purifies biomaterial x, the second biomaterial y, the third biomaterial z, and so on. X, y and z may represent the same or different biomaterials to be purified. A solution containing all biomaterials passes through each system containing bead loops which circulate low porosity particles having chemical hooks which specifically bind either x, y, or z, and so on. After the solution has passed through all of the beads loops and x, y, and z biomaterials have been removed within each of the specific bead loops, the bead loops are disconnected from each other and each loop system is separately processed to yield purified biomaterials x, y, and z.

It should be appreciated that the method and system of the present invention is capable of being incorporated in the form of a variety of embodiments, only a few of which have been illustrated and described above. The invention may be embodied in other forms without departing from its spirit or essential characteristics. The described embodiments are to be considered in all respects only as illustrative and not restrictive and the scope of the invention is, therefore, indicated by the appended claims rather than by the foregoing description. All changes that come within the meaning and range of equivalency of the claims are to be embraced within their scope.

We claim:

1. A system for affinity separation of a target compound from a fluid comprising:
   a) a static filtration apparatus comprising a housing having a feed port, a concentrate port, a filtrate port, and a filtration medium disposed within the housing:
   b) the feed port and the concentrate port being in fluid communication with the upstream side of the filtration medium, while the filtrate port is in fluid communication with the downstream side of the filtration medium; and
   c) a suspension comprising a plurality of low porosity, low non-specific binding, reconstituted cellulose affinity particles having a ligand grafted thereon and a fluid containing a sheer sensitive target compound to be isolated possessing an affinity for the ligands fed into the filtration apparatus via the feed port for intermixing.

2. The system of claim 1, wherein said low porosity affinity particles are nonporous.

3. The system of claim 2, wherein said low porosity affinity particles have an average diameter at least about two-fold larger than the average pore size of said filtration medium.

4. The system of claim 3, wherein said fluid contains particles and said filtration medium has an average pore size at least about five-fold larger than the size of the largest particulate in said fluid.

5. The system of claim 2, wherein said low porosity affinity particles have an average diameter at least about five-fold larger than the average pore size of said filtration medium.

6. The system of claim 1, wherein said low porosity affinity particles are generally spherical.

7. The system of claim 6, wherein said fluid contains particles and said filtration medium has an average pore size at least about two-fold larger than the size of the largest particulate in said fluid.

8. The system of claim 1, wherein said low porosity affinity particles are generally identical in diameter.

9. The system of claim 1, wherein said low porosity affinity particles have an average diameter of about 120 um or less.

10. The system of claim 9, wherein said filtration medium has an average pore rating of less than about 5 um.

11. The system of claim 1, wherein said low porosity affinity particles have an average diameter of about 60 um or less.

12. The system of claim 1, wherein said low porosity affinity particles have an average diameter or about 20 um or less.

13. The system of claim 1, wherein said low porosity affinity particles have an average diameter of between about 1 and about 3 um.

14. The system of claim 1, wherein said filtration medium is a microporous membrane having an average pore rating of less than 1 um.

15. The system of claim 1 wherein said low porosity affinity particles have a plurality of chemical linkers attached thereto.

16. The system of claim 1 wherein said low porosity affinity particles are linker-coated polystyrene affinity particles having generally less than 40% porosity.

17. A system for affinity separation of a target compound from a fluid comprising:
   a) a static filtration apparatus including a housing having a feed port, a concentrate port, a filtrate port, and a filtration medium disposed within the housing;
   b) the feed port and the concentrate port being in fluid communication with the upstream side of the filtration medium, while the filtrate port is in fluid communication with the downstream side of the filtration medium; and
   c) a suspension comprising a plurality of low porosity, low non-specific binding, reconstituted cellulose affinity particles having a ligand thereon and a sheer sensitive target, the affinity particles capable of binding the sheer sensitive target, wherein the suspension containing affinity particles with bound target is fed into the filtration apparatus via the feed port.

* * * * *